United States Patent [19]

Block

[11] Patent Number: 5,321,265
[45] Date of Patent: Jun. 14, 1994

[54] NON-INVASIVE TESTING

[76] Inventor: Myron J. Block, 334 N. Main St., P.O. Box 148, North Salem, N.H. 03073

[21] Appl. No.: 914,265

[22] Filed: Jul. 15, 1992

[51] Int. Cl.⁵ .......................................... G01N 21/35
[52] U.S. Cl. ................................. 250/343; 356/405
[58] Field of Search ............ 250/339, 340, 341, 343; 356/405

[56] References Cited

U.S. PATENT DOCUMENTS 4,278,538 7/1981 Lawrence et al. ................ 356/405
5,028,787 7/1991 Rosenthal et al. ................ 250/341

FOREIGN PATENT DOCUMENTS

0233873 3/1986 German Democratic Rep. ................................ 356/405
1187032 10/1985 U.S.S.R. ............................ 356/405

Primary Examiner—Paul M. Dzierzynski
Assistant Examiner—Richard Hanig

[57] ABSTRACT

A new non-invasive detection method for glucose and other constituents of interest in a sample has been developed. The apparatus and methods of the invention provide an analog of color perception of human vision, preferably in the near infrared region, replacing spectrophotometers and narrow band sources used in other noninvasive near infrared detection methods. A plurality of detector units are used, each covering a broad and overlapping region of the detected spectrum, paralleling color perception and colorimetry. In some circumstances, a neural net is used for analysis, allowing the system to learn. A novel method for background discrimination is also described.

29 Claims, 4 Drawing Sheets

NON-INVASIVE TESTING

BACKGROUND OF THE INVENTION

The present invention concerns the testing for constituents of interest using radiation, preferably near infrared radiation. More particularly, an apparatus and a method of testing for constituents such as glucose, alcohol, drugs of abuse or other materials in a non-invasive manner have been developed. These methods are particularly well adapted for use in the home glucose testing market since they do not require a finger puncture to obtain a separable blood sample but rather can be utilized without bodily invasion.

Development of non-invasive testing method has become an important topic in the last several years. The spread of acquired immunodeficiency disease syndrome (AIDS), and the associated fear among public and healthcare personnel of AIDS has made many people afraid of invasive procedures. "Invasive procedures," as used herein are procedures where a sample such as blood is taken from the body by puncture or other entry into the body before analysis, while non-invasive procedures do not require bodily penetration. Not only can diseases such as AIDS be spread with invasive procedures if proper precautions are not followed, hepatitis and other similar blood diseases are more common problems in this type of testing. For example, a recent article, "Nosocomiel transmission of Hepatitis B virus associated with the use of a spring-loaded finger-stick device," *New England Journal of Medicine* 326 (11), 721-725 (1992), disclosed a mini-hepatitis epidemic in a hospital caused by the improper use of an instrument for taking blood samples. The nurses were unintentionally transmitting hepatitis from one patient to another with the sampling devise itself. This type of disease transfer is eliminated with non-invasive testing.

The diabetic population has also been clamoring for non-invasive test instruments. Many diabetics must test their blood glucose levels four or more times a day. The modern battery powered instruments for home use require a finger prick to obtain the sample. The extracted blood sample is then placed on a chemically treated carrier which is inserted into the instrument to obtain a glucose reading. This finger prick is painful and can be a problem when required often. In addition, although the price has dropped considerably on these instruments, the cost for the disposables and the mess and health risks associated with having open bleeding is undesirable.

Accordingly, a number of groups have recently tried to make non-invasive instruments for testing a variety of analytes, particularly glucose. A recent trend in non-invasive testing has been to explore the use of the near infrared spectral region (700-1100 nm). This region contains the third overtones for the glucose spectrum and eliminates many of the water bands and other inference bands that are potential problems for detection. However, this work has been carried out using classic spectrophotometric methods such as a set of narrow wavelength sources, or scanning spectrophotometers which scan wavelength by wavelength across a broad spectrum. The data obtained from these methods are spectra which then require substantial data processing to eliminate background; accordingly, the papers are replete with data analysis techniques utilized to glean the pertinent information. Examples of this type of testing includes the work by Clarke, see U.S. Pat. No. 5,054,487; and Primarily the work by Rosenthal et al., see e.g., U.S. Pat. No. 5,028,787. Although the Clarke work uses reflectance spectra and the Rosenthal work uses primarily transmission spectra, both rely on obtaining near infrared spectrophotometric data.

One problem with using these types of methods is that spectrophotometers were conceived primarily for accurate determination in terms of wavelength, of the spectral structure, rather than for discriminating the presence of weak broadband features in strong broadband backgrounds. Since in non-invasive testing for glucose and other materials the primary information sought is the concentration, those using spectrophotometric methods here had to resort to using a number of unsatisfactory analysis techniques to suppress unwanted interferences and to calculate the amplitude of the signal.

The Rosenthal U.S. Pat. No. 5,028,787 (the Rosenthal '787 Patent) illustrates this type of analysis technique for glucose testing using near infrared spectrophotometric methods.

Figure 1:
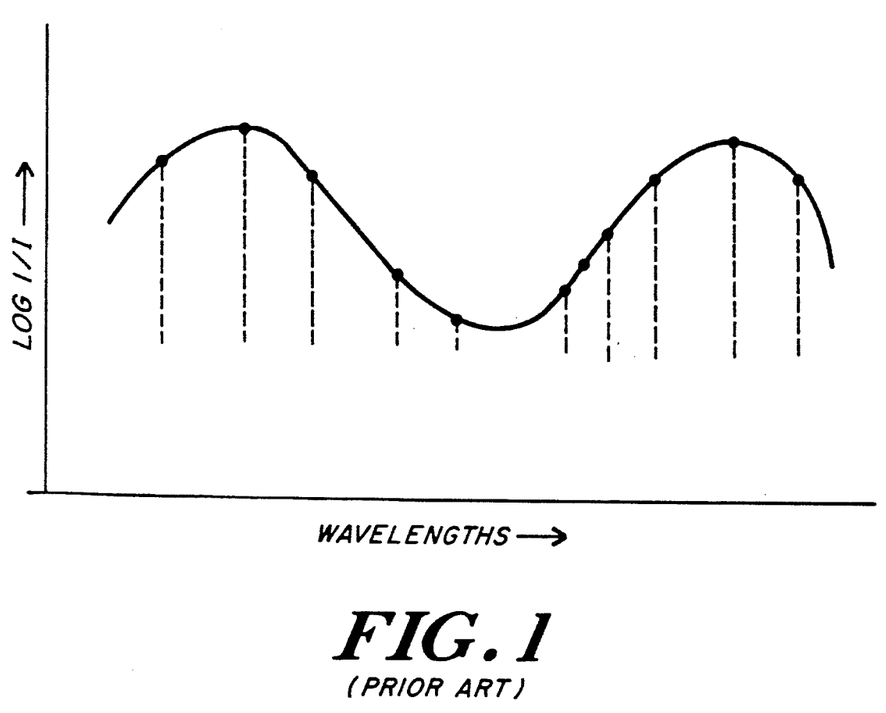
FIG. 1 is a spectrum for non-invasive glucose testing taken from U.S. Pat. No. 5,028,787.

First, a scan is made of 10 gl/$_I$ vs. wavelength and the raw data is analyzed. FIG. 1 of the present application is just such a plot, taken from the Rosenthal '787 Patent. Rosenthal takes the data developed from this scan and analyzes it using first and second derivative equations in an attempt to obtain meaningful information. Additional patents and articles by Rosenthal, Cavinato, and others have used similar techniques for determinations of levels of fat, ethanol, and other constituents of interest in a variety of samples.

However, all these techniques are dependent on the discrimination of the spectrophotometric data obtained. No form of data analysis can add to the initial information gathered; it can only put the measured information in a form which deemphasizes certain items of interference arising from the background or other constituents which make analysis of the sample difficult. A better solution to the problems of interference in broadband spectra is rather to obtain different raw data by measuring different aspects of the phenomenon.

As noted, FIG. 1 is a plot of 10gl/$_I$ vs. wavelength, taken using a scanning spectrophotometer. The scanning spectrophotometer takes a series of discrete, single wavelength intensities and presents them as a function of time to obtain the spectrum. A plurality of high resolution features are necessary to obtain meaningful information. However, the spectra of analytes of present interest do not include the large high resolution structures of classical infrared spectroscopy but rather have a few low resolution features with much of the information contained in the intensity. As such, these spectra appear more like the reflection spectra of colored objects in the visible region. A detection device optimized for analysis of this type of spectra would provide better discrimination.

Human vision is a incompetent spectrophotometer but is superb at the subtlest color discrimination and identification even under greatly varying illumination. The present invention measures or obtains the raw data in the infrared in a manner more similar to the way the eye Performs in the visible, than classic spectrophotometric measurements. While visual perception is very complex and not completely understood, one approach suggested is the obtaining and processing of the raw data as closely as possible to the known aspects of color perception, utilizing a succession of steps or processing levels. Each step itself provides a useful product and succeeding steps represent products of greater capability.

Figure 2:
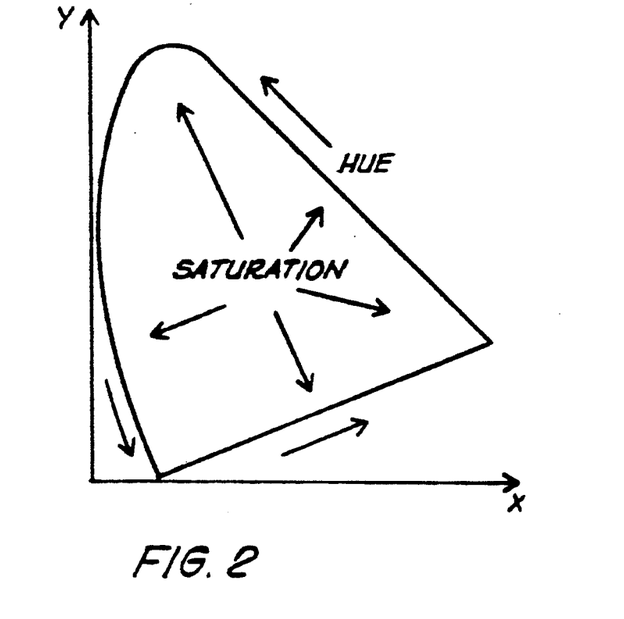
FIG. 2 is a CIE 1931 chromaticity plot.

The first step is the analog of colorimetry. Colorimetry is numerical color communication. This numeric approach uses three dimensions to describe the color. There presently are several such three dimensions spaces in use. One of these three dimensional spaces is the CIE 1931 (x,y)-chromaticity diagram (See FIG. 2). Luminosity, the third dimension, is not shown in FIG. 2. It is the trivariant nature of color vision that permits color to be specified in a three dimensional space.

Figure 3:
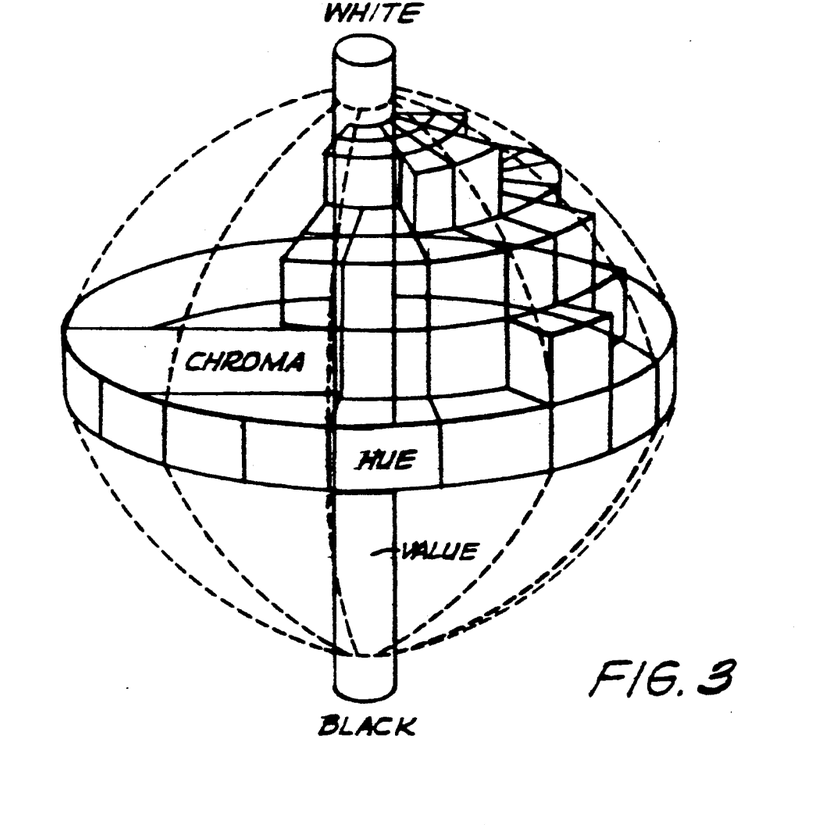
FIG. 3 is a three dimensional plot of color in terms of hue, chroma and value.

Another three dimensional space is represented in FIG. 3. A plot is made of hue, chroma and value and is shown as a three dimensional solid. These three numerical values can be used to specify any perceived color.

It is most important to note that although it is convenient to describe color in terms of a colorimetry, this is not color perception. Color perception is much more complex. However colorimetry is useful for color matching under specific conditions. An analog of colorimetry, particularly one in the infrared region, would show similar usefulness in determining analyte concentration.

There are commercially available colorimeters in the visible for measuring tristimulus values in terms of luminosity, hue and saturation. Briefly, these colorimeters use three detectors, with each detector input being filtered with a different filter function. Each of the filter functions is chosen to be similar to the three absorption spectra of the pigments of the three color receptive cones of the human retina. However, it appears no one has used, or even considered the use, of an analog of color perception for concentration measurements or even applied the method of colorimetry to infrared measurements as described herein.

Similarly, noninvasive measurement of arterial oxygen saturation by pulse oximetry is widely acknowledged to be one of the most important technological advances in clinical patient monitoring. Pulse oximeters measure differences in the visible and near infrared absorption spectra of fully oxygenated and reduced hemoglobin in arterial blood. Unlike clinical blood gas analyzers, which require a sample of blood from the patient and can only provide intermittent measurement of patient oxygenation, pulse oximetry provide continuous, and instantaneous measurement of blood oxygen levels.

However, current commercial oximeters, and their algorithms are inaccurate under conditions of low pulse pressure and/or low oxygen saturation. These severe conditions are observed in the normal unborn fetus. Unlike the transmission sampling of the commercial oximeters, space limitations associated with the fetus require that the spectral data be obtained by reflectance sampling. Reflectance sampling results in spectral data with a significantly lower signal-to-noise ratios than obtained with transmission sampling. It has been suggested that a new analysis technique using multivariate calibration methods can improve the precision, accuracy and reliability of quantitative spectral analysis. Even these techniques are limited by the type of input data.

Accordingly, an object to the invention is to provide an apparatus which provides an analog of colorimetric detection units so as to allow the measurements of the concentration of a constituent of interest.

Another object of the invention is to provide a method of measuring constituents of interest in a sample, preferably in a non-invasive manner, which is accurate, inexpensive and quick using an analog of a colorimetric analysis.

Another method of the invention is to provide a handheld instrument for glucose or drugs of abuse measurement based on the application of colorimetric type measurements to the near infrared region.

These and other objects and features will be apparent from the description and the accompanying drawing.

SUMMARY OF THE INVENTION

The present invention features an apparatus and method for the measurement of concentration of a constituent in a sample using reflectance or transmission, particularly in the near infrared. The apparatus and method of the present invention provide rapid, inexpensive measurements of high accuracy and are particularly adapted for non-invasive testing of the human body for constituents such as glucose or drugs of abuse.

In more detail, the invention provides an apparatus for measurement of the concentration of a constituent of interest which has absorbance or reflectance bands in the visible or near infrared spectrum. The constituent is in a sample which is illuminated by a light source that generates broad spectrum, preferably near infrared, radiation. Although a single light source is preferred, in some embodiments multiple light sources can be used if the additive output of the light sources as a whole provides the requisite spectrum.

The apparatus also includes a sample chamber for holding the sample during measurement. The sample chamber can be arranged for non-invasive measurements of a portion of the human body such as a finger. The apparatus further includes detection means in the form of a plurality of detector units. Each detector unit is responsive to a specific region of the illuminating radiation or spectrum. Each of the detector units have at least partial non-parallel overlapping regions of spectral response with at least one other of the detector units. In this manner, even in the region where the response of detector units overlap, each unit can provide some distinct information. The response from the detector units is the form of an output signal which is then transmitted to analysis means for combining and converting the output signal into a measure of the concentration of the constituent of interest.

One key to the present invention is the realization that the detector units used should have a response to either transmitted or reflected radiation from the sample which is in a form of an analog of the color response of the eye. The response of the eye is in terms of red, green and blue sensors, the output of which are processed by the neural net in the eye and by the brain to provide the perception of color. The simplest approximation of color perception for certain specific conditions is colorimetry. A near infrared analog of colorimetry, using infrared rather than visible radiation, is proposed herein, as are the use of colorimetry for concentration measurements and improved analysis methods. Accordingly, preferred embodiments of the invention have at least three detector units each having a spectral detection range centered about a different portion of the selected spectrum but with response bands sufficiently wide that there is some overlap with at least one, and preferably more than one, other of the detector units. The detection means may also include a black/white or luminosity detector which is responsive to entire spectrum for which the other detector units have a spectral response. This "black/white" or luminosity detector, as used herein, is a detector like the other three that measures intensity of the signal photometrically in its spectral region of interest without Perceiving the specificity of the wavelength, thereby showing the presence of a signal at one (or more) of the three other detectors.

The second step in complexity is to more closely approach color perception by using computational methods operating on the outputs of the detector units to emphasize the analyte with respect to the background. As a start, the computational models of color vision that have been developed in the field of "artificial intelligence" for attempting to achieve machine color vision will be utilized.

The third step towards approaching an analog of human color perception is to feed the detector unit outputs into an artificial neural net assembled similarly to the neural organization or circuitry of the retina and color portions in the brain. Here we expect to achieve learning for the detection, quantification, and in particular signal discrimination against background, with a smaller component cost and small size.

Neural networks, in the form of chips and other hardware, are presently available. Neural networks (or nets) provide processing which is similar to the brain (albeit on a less complicated scale) and, as such, can be "taught" to eliminate certain items of background.

The detector units can be selected to absorb only a particular broad band spectral region but more easily, standard silicon photocells can be used in conjunction with a series of broad bandpass filters. The term "broad bandpass infrared filters", as used herein, means filters that have a substantial half-width about a central wavelength, e.g., specified wavelengths in the near infrared region, so as to pass significant amounts of radiation for several hundred nm about the central wavelength. The use of broad bandpass filters allows significant response "tails" which overlap.

The apparatus can be adapted for detection of many substances. Preferred constituents of interest include glucose and drugs of abuse. "Drugs of abuse," as defined herein, include not just classic drugs of abuse such as marijuana, heroin, cocaine, amphetamines, barbiturates and other hallucinogenic or mind altering drugs, but also alcohol. For purposes of the invention, it does not matter whether the glucose or drug of abuse is measured directly but rather solely that the measurement of the sample can be correlated to the concentration of the constituent of interest. For example, it may be that the glucose is always correlated with the presence of a particular carrier or other indicating constituent and the carrier or constituent is measured in addition to and/or instead of the glucose itself.

The invention also features a method for measuring the concentration of a constituent of interest which absorbs or reflects light. The method has the steps of illuminating the sample with broadband spectrum, preferably near infrared, radiation and detecting transmitted or reflected radiation from the sample. At least one signal corresponding to the detected radiation is generated and analyzed to determine the concentration of the constituent of interest. The detecting step of the method includes impinging radiation transmitted or reflected from the sample onto a detection array which includes a plurality of detector units each of which is responsive to a specific region of the near infrared spectrum. The specific spectral response from each detector unit partially overlaps, in a non-parallel manner, the response from at least one other detector unit. Preferably, there are at least three detection units, each of which has a peak spectral response in a separate portion of the near infrared spectrum. The analysis step using this type of detection array allows analysis such that the output is formed into an analog of a colorimetric (e.g., tristimulus) values. The detector units may include broad bandpass filters to provide this spectral response and the detector array may also include a black/white detector unit such as has previously been described. In another aspect of the invention, the analysis may use an analog of a neural network, paralleling the working of the eye and brain. This neural net based apparatus may even be used for classic colorimetry measurements.

The method of the invention is particularly well suited to non-invasive testing for constituent of the human body such as glucose, a glucose indicator or a drug of abuse. The finger is the preferred region for a sample for non-invasive testing.

Another aspect of the invention is the use of paired detectors for referencing. In present non-invasive methods, there is no way to obtain a control reporting a "zero" concentration of the constituent of interest. However, by using a simulating filter or a filter made of the same material as the analyte but which has a concentration of the constituent of interest that is much higher than that in the sample, changing amounts of constituent in the sample merely cause a minor perturbation in the measurements from that "high concentration" reference detector. It may also be possible to use a material with substantially identical absorbance (or reflective) characteristics in place of the high concentration filter.

By using paired detectors with the "high concentration" filter in front of one detector of the prior, one can obtain background measurements, unperturbed by the presence of the analyte to enhance discrimination. The term "paired detectors," as used herein means two or more detectors which are identical except for the high concentration filter. For example, there could be paired red analog detectors, paired green analog detectors and paired blue analog detectors, with the only difference being the addition of the high concentration filter to one of each pair. This type of high concentration filter is not limited to use with the apparatus and methods described previously but has general applicability to any spectrophotometric system.

The following detailed description and the drawing will more clearly delineate the invention.

DETAILED DESCRIPTION OF THE INVENTION

The present invention provides non-invasive procedures which can be used to test for glucose or other substances so long as the constituent of interest has absorption or reflectance bands in a selected, preferably, near infrared, spectrum. The apparatus and methods of the invention are based in part, on the recognition that the present problems associated with attempting to conduct non-invasive measurements using near infrared radiation relate to the type of information which is obtained using spectrophotometers. Although using different analysis techniques can clarify what information has been obtained, these analysis techniques cannot generate optimum results if the underlying information obtained is itself not optimum. By applying an analog to colorimetry to concentration measurements, particularly forming a near infrared parallel of the three different pigments of the cones of the retina, significant information can be obtained which relates to concentration. Since in color perception "color constancy" is maintained under extreme variations in illumination, the use of neural networks or digital computation to provide information in a manner more similar to the information processing of the eye-brain is preferred.

As noted previously, classic spectrophotometric methods for non-invasive measurements require the use of complex, and not altogether successful, data handling techniques in order to obtain meaningful information. FIG. 1, which is a plot of wavelength versus 1/I intensity made using a scanning spectrophotometer for a non-invasive determination of glucose, shows the problem with the classic techniques. First, the scan takes sufficient time that there is the possibility of a change in the test conditions during the scan. Second, while spectrophotometric measurements in the near infrared region are useful when there are high resolution features so that the substance of interest can be clearly discriminated from other substances, they do not work well unless the background and the features are separable. When glucose absorption bands are sought in the near infrared region, particularly using non-invasive techniques, only a few, low resolution features occur and the spectrum, such as that shown in FIG. 1. This spectra most resembles the spectrum of a colored object.

Figure 4:
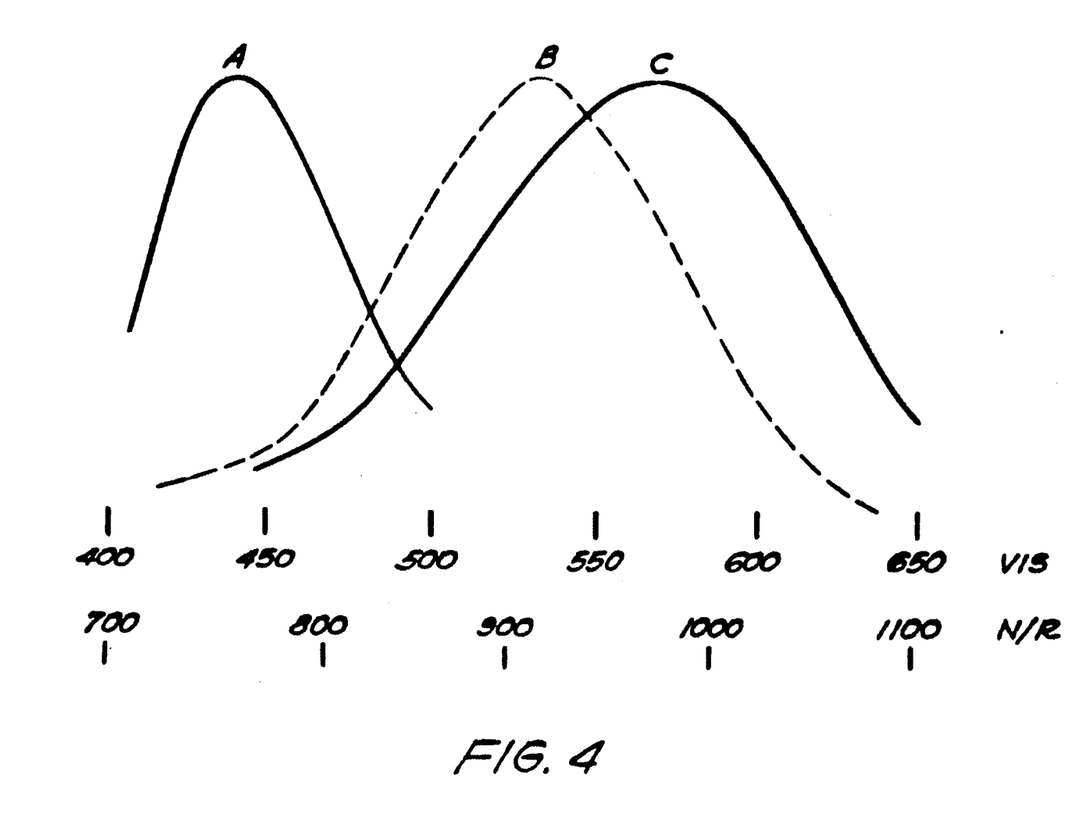
FIG. 4 is a blue, green and red detector response vs. wavelength for a standard colorimeter, with a second scale of near infrared wavelengths as well as the visual wavelengths imposed on the X axis.

FIG. 4 shows just such a color spectrum, with the red, green and blue detector responses of a colorimeter. The information determined from a colorimetric measurements is often used to determine the absolute color, and color differences of particular samples and their illuminants. Portable, inexpensive colorimeters are available in the market. For example, Minolta makes a series of tristimulus colorimeters including the Chroma meter xy-1 and Chroma meter CL-100. These tristimulus colorimeters may be used alone or attached to a data processor such as the Minolta DP-100 to express chromaticity readings in $Y_{xy}$ or $Y_{u'v'}$ systems, color difference readings in terms of $\Delta(Y_{xy})$ or $\Delta(Y_{u'v'})$, luminescence, or black body temperature. These units can be used for either static or flickering light sources. Other instruments may be faster, i.e., give even more readings per second.

The Minolta colorimeters use silicon photocells which are filtered with red, green and blue broadpass filters. These filters cover a range from about 400-650 nm.

One aspect of the present invention utilizes this type of colorimeter with its filters replaced with filters having similar transmission and absorbance shapes but in the near infrared rather than visual region. The lower indices on the x-axis of FIG. 4, those designated near infrared, can be used for guidelines for analogous transmission spectra of filters for silicon photocells to obtain a spectral response in the near infrared rather than visual region. In this way, a near infrared equivalent to the tristimulus values could be constructed. With such information and sufficient standards, non-invasive measurements of constituent of interest such as glucose could be carried out in the near infrared region using substantially similar apparatus.

Figure 5A:
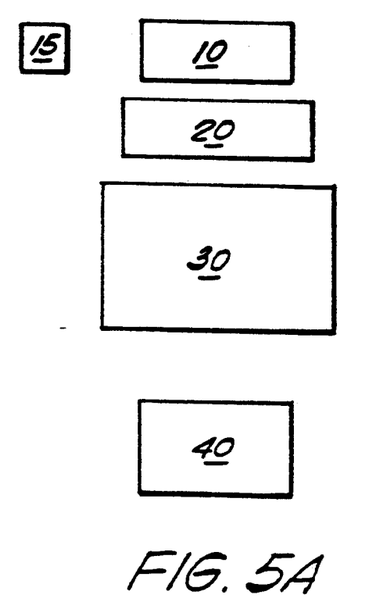
FIGS. 5A and 5B are variations of apparatus useful in the present invention.

FIG. 5A shows one type of apparatus particularly useful for non-invasive test of glucose using the methods of the present invention. A light source 10, which provides broad spectrum near infrared radiation (e.g., 700-1100 nm), is used for illumination. One possible light source is a tungsten-halogen bulb in a quartz envelope, filtered with a "heat shield" 20, if necessary, to provide only this wavelength range. A sample chamber 30 is shown for insertion of a finger or other bodily part if measurements are going to made on a human or animal body. If a non-body sample is to be used, for example an agricultural sample, a different shaped sample chamber could be used in the same location. The heat shield 20, which is optionally placed between lamp 10 and sample chamber 30, can be any material which will reduce the heat generated by the lamp 10 before if reaches sample chamber 30 without significantly degrading or absorbing the light generated from lamp 10 in its measurement region.

A detection array 40 is placed on the side of sample chamber 30 furthest from lamp 10 if a transmission mode is being utilized or off to the side of lamp 10 if a reflectance mode is being utilized.

Figure 5B:
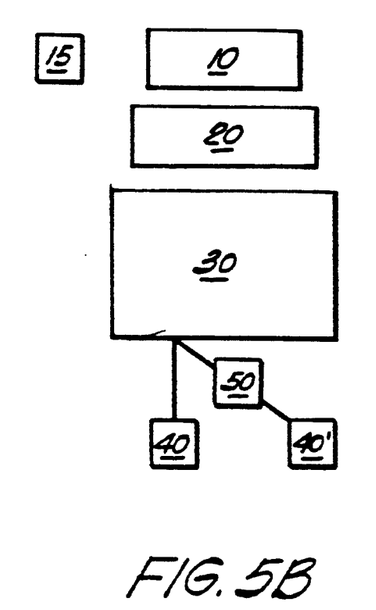

Source reference detectors 15 may be used to both measure the near infrared "color" of the source and guard against any changes in source output. In some embodiments, a paired detector array 40' and a special filter 50 may also be used. FIG. 5B shows the same apparatus as FIG. 5A except the paired detectors are present. The illumination transmitted from sample chamber 30 goes to beam splitter 60 then either directly to detector array 40 or through filter 50 then to detector array 40'. Filter 50 is, preferably, a filter containing the same constituent of interest as is in the sample but in a concentration which is much (e.g., several order of magnitudes) higher. As such, filter 50 provides significant information concerning the background and the effective sample thickness since the amount of the constituent of interest in the sample acts merely as a negligible perturbation. This type of filter 50 is also useful for any other type of spectrophotometric analysis. The effective sample thickness or effective pathlength may also be corrected for by measuring the absorption of the sample in a wavelength region dominated by the absorption of the liquid carrier; e.g., water. The light reflected or transmitted from the sample is split into two output beams, a first output beam which is incident on a first detector responsive to the wavelength of the sample identifying bands, and the second output beam which is incident on a second detector primarily responsive to liquid carrier absorption bands. This liquid carrier absorption measurement follows the same path as the sample indicating bands, yields an effective pathlength correction factor.

Figure 6:
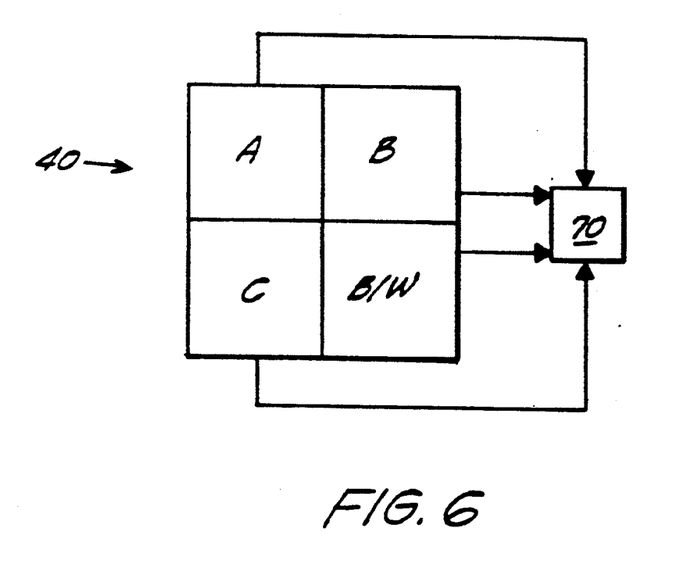
FIG. 6 is a detection array useful in the present invention.

FIG. 6 shows one type of detection array 40 which may be used in the present invention. This detection array has four detector units, three which are filtered in such a way that they have different peak spectral response but some partial overlap of spectral response while the fourth detector constituents a black/white detector. This black/white detector is responsive to all wavelengths in the infrared measurement region for which the other three detectors are responsive; that is, it generates in output signal responsive to wavelengths which cause a response for any of the three other detectors. As such, it acts like the rods of the retina of the eye.

The output from detector 40 (and detector 40' if used) is fed to analysis means 70. Analysis means 70.can be a computer, hardwired logic circuits, or a neural network. In any case, this analysis means 70 converts the output signal from the detectors to a measure of concentration.

Once the data from the detectors is obtained, it can be treated in a variety of ways. As noted previously, an analog of a colorimetric tristimulus values can be produced and calibrated against known glucose concentrations. Problems that may arise with this simple type of data analysis is that calibration may be frequently required and may not be sufficiently universal, in that it will lack the analog of "color constancy" as do all colorimeters.

However, the data analysis from the system, can be improved to more closely approach color perception by digital computation or with the use of neural networks (neural nets). While artificial neural networks usually contain hundreds of interconnected neurons, this analog of color perception may only require about two dozen.

What this artificial neural act attempts to simulate are:

1. The horizontal cells, which transmit signals horizontally from the rods and cones to the bipolar cells.

2. The bipolar cells which transmit signals from the rods, cones and horizontal cells to synapse with either amacrine cells or ganglion cells.

3. The amacrine cells which transmit signals in two directions, either directly from bipolar cells to ganglion cells or horizontally among the axons of the bipolar cells, the dendrites of the ganglion cells, and/or other amacrine cells.

4. The ganglion cells which transmit output signals through the optic nerve to the brain.

5. The interplexiform cells which transmit signals in the retrograde direction from the inner plexiform layer to the outer plexiform layer. The signals from these cells are all inhibitory.

6. Brain cells associated with "blobs" which are believed to allow for color constancy.

7. Brain cells which enable binocular fusion of colors. That is, when the fovea of one eye is stimulated by homogenous red light and the fovea of the other eye is stimulated by homogenous green light, the resultant binocular impression is the same as that of seeing yellow.

The most important factor of using a neural network is the learning capacity of the network. Since the neural network can "learn", it may be calibrated a single time for the individual, or even have a universal calibration at the factory, and still give consistent results over time. Learning in a neural net context is provided by a change in the way of connections run from one "neuron" to another.

The foregoing description invention is meant to be explanatory only and not intended to be limited to the scope of the invention. The invention is defined by the following claims.

What is claimed is:

1. An apparatus determining the concentration in a sample of a constituent of interest which has absorption or reflectance bands in a selected region of the spectrum comprising:

a light source that illuminates said sample with broad spectrum radiation in said selected region;

a sample chamber for confining said sample during said illumination;

detection means in the form of a plurality of detector units, each of said detector units being responsive to a specific region of said spectrum and having a partial overlapping region of spectral response with another of said detector units, said response from each detector unit being in the form of an output signal; and analysis means for converting said output signals into a measure of said concentration.

2. The apparatus of claim 1 wherein said selected region of said spectrum is the near infrared region.

3. The apparatus of claim 1 when said detector means comprises at least three detector units each having a spectral response region centered about a different portion of said spectrum.

4. The apparatus of claim 3 wherein said detector units each generate signals that are near infrared analogs of the color receptive elements in vision.

5. The apparatus claim 4 wherein said analysis means generates an output which is a near infrared analog of a location in a colorimetric three dimensional space.

6. The apparatus of claim 3 wherein said detection means further comprises a black/white luminosity detector which is responsive to and overlaps the near infrared spectral response of said detector units.

7. The apparatus of claim 1 wherein said analysis means comprises an artificial neural network.

8. The apparatus of claim 1 wherein each of said detector units comprises broad bandpass filters.

9. The apparatus of claim 1 wherein said detector units comprise silicon photocells.

10. The apparatus of claim 1 wherein said sample chamber is arranged for non-invasive measurements on a portion of a human body.

11. The apparatus of claim 10 wherein said human body portion comprises a finger.

12. The apparatus of claim 10 wherein said constituent of interest is selected from the group consisting of glucose, and glucose indicating constituents.

13. The apparatus of claim 11 wherein said constituent of interest is selected form the group consisting of drugs of abuse, and drugs of abuse indicating constituents.

14. The apparatus of claim 1 further comprising a filter unit which has an absorption at the same spectral bands of said constituent of interest, the absorption of said filter unit corresponding to at least one order of magnitude greater concentration than the response of said constituent of interest.

15. The apparatus of claim 14 wherein said filter unit comprises a high concentration solution of said constituent of interest.

16. A method for measuring the concentration in a sample of a constituent of interest which absorbs or reflects light , said method comprising the steps of:

illuminating said sample with broad spectrum radiation;

detecting transmitted or reflected radiation from said sample;

generating at least one signal corresponding to said detected radiation; and analyzing said signal to measure the concentration of said constituent;

wherein said detecting step includes impinging the radiation transmitted or reflected from said sample onto a detection array which generates said signal, said detection array including a plurality of detector units each responsive to a specific region of the transmitted or reflected spectrum, the spectral response of each of said detector units having at least partial overlap with the response of at least one other of said detector units.

17. The method of claim 16 wherein at least three detection units are used in said detecting step, each detector unit having a peak spectral response in a separate portion of said spectrum.

18. The method of claim 17 wherein said analysis step comprises forming from the output a near infrared analog of a specific position in a three dimension colorimetric space.

19. The method of claim 16 wherein said detector units comprise broad bandpass filters.

20. The method of claim 16 wherein said detecting step further comprises the use of a black/white detector unit which is responsive to the entire spectrum for which said detector units have a spectral response.

21. The method of claim 16 wherein said analysis step comprises utilizing an artificial analog of a neural network.

22. The method of claim 21 wherein said artificial neural network is calibrated and trained to process said signals to achieve an analog of color constancy in vision.

23. The method of claim 16 wherein said method is used for non-invasive testing for a constituent in a human body.

24. The method of claim 23 wherein said constituent is related from the group consisting of glucose and glucose indicating constituents.

25. The method of claim 23 wherein said constituent is selected form the group consisting of drugs of abuse and drugs of abuse indicating constituents.

26. The method of claim 23 wherein said sample comprises a finger.

27. An apparatus to perform colorimetry using absorption or reflectance in a selected region of the spectrum comprising:

a light source that generates broad spectrum radiation in said selected region;

detection means in the form of a plurality of detector units, each of said detector units being responsive to a specific region of said spectrum and having a partial overlapping region of spectral response with another of said detector units, said response from each detector unit being in the form of an output signal; and analysis means in the form of a neural net for converting said output signals into colorimetry values.

28. A method for colormetric measures using transmittance or reflectance measurements comprising the steps of:

illuminating a sample with broad spectrum radiation;

detecting transmitted or reflected radiation from said sample;

generating at least one signal corresponding to said detected radiation; and analyzing said signal to measure the concentration of said constituent;

wherein said detecting step includes impinging the radiation transmitted or reflected from said sample onto a detection array which generates said signal, said detection array including a plurality of detector units each responsive to a specific region of the transmitted or reflected spectrum, the spectral response of each of said detector units having at least partial overlap with the response of at least one other of said detector units;

and said analysis step is carried out using a neural net.

29. The method of claim 28 wherein said method is used to achieve substantial color constancy.

* * * * *